United States Patent [19]

Etschenberg et al.

[11] 4,285,935

[45] Aug. 25, 1981

[54] DEHYDROPEPTIDE COMPOUNDS, THEIR PRODUCTION AND THEIR MEDICAL USE

[75] Inventors: Eugen Etschenberg, Cologne; Haireddin Jacobi, Leichlingen; Wolfgang Opitz, Cologne, all of Fed. Rep. of Germany

[73] Assignee: Bayer Aktiengesellschaft, Leverkusen, Fed. Rep. of Germany

[21] Appl. No.: 114,468

[22] Filed: Jan. 23, 1980

[30] Foreign Application Priority Data

Feb. 7, 1979 [DE] Fed. Rep. of Germany ....... 2904512

[51] Int. Cl.[3] ..................... A61K 37/00; C07C 103/52

[52] U.S. Cl. .............................. 424/177; 260/112.5 R

[58] Field of Search .................. 424/177; 260/112.5 R

[56] References Cited

PUBLICATIONS

Katrukiha, et al., Chem. Abst. 92, (1980) 6926c.

*Primary Examiner*—Delbert R. Phillips

*Attorney, Agent, or Firm*—Sprung, Felfe, Horn, Lynch & Kramer

[57] ABSTRACT

This invention relates to dehydropeptides containing a tryptophan moiety useful as tumour-resolving and/or histolytic medicaments. Also included in the invention are methods for the preparation of said dehydropeptides, compositions containing said dehydropeptides and methods for the use of said dehydropeptides and dehydropeptide compositions.

15 Claims, No Drawings

DEHYDROPEPTIDE COMPOUNDS, THEIR PRODUCTION AND THEIR MEDICAL USE

The present invention relates to certain new dehydropeptide compounds, to a process for their production and to their use as histolytic medicaments.

Some dehydrooligopeptides and their tumor-resolving or histolytic action are already described generally in DOS (German Published Specification) No. 2,659,114 and DOS (German Published Specification) No. 2,659,154; however, the value of the compounds listed in these Specifications is limited, since on local administration they cause severe pain, suppression of which is only incomplete even when analgesic agents are simultaneously administered.

According to the present invention there are provided compounds which are dehydropeptides of the general formula

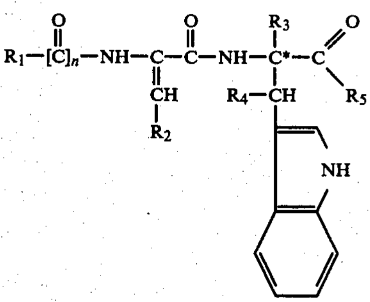

or a salt thereof, in which $R_1$ denotes a hydrogen atom, an optionally substituted alkyl, alkenyl, aralkyl, aralkenyl aryl, alkoxy group or a heterocyclic ring, $R_2$ denotes a phenyl radical which is optionally substituted by alkyl, aryl, alkoxy, hydroxyl, nitro, amino, acylamino or halogen, $R_3$ and $R_4$ both denote a hydrogen atom, or together denote an additional bond between the two carbon atoms, $R_5$ denotes a hydroxyl group or an optionally substituted alkoxy, aralkoxy or amino group and n is 1 or 0, and in which, when $R_3$ and $R_4$ both denote a hydrogen atom, the centre of asymmetry C* at the substituent $R_3$ is in the racemate form or in the D-form or L-form.

Racemate mixtures can be separated into the pure racemates in a known manner on the basis of the physiochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diasteromers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing staring substances, containing one or more asymmetrical C atoms, in the form of the pure racemates or optical antipodes.

In the disclosure herein above and hereinbelow, unless otherwise specified, alkyl or alkenyl contains up to 8 (preferably up to 4) carbon atoms; aralkyl and aralkenyl are preferably mono- or bi-cyclic carbocyclic in the "aryl" portion (e.g. phenyl, biphenyl, naphthyl) and contain up to 8 (preferably up to 4) carbon atoms in the alkyl or alkenyl portion; aryl is preferably mono- or bi-cyclic carbocyclic (e.g. phenyl, biphenyl, naphthyl); alkoxy contains up to 8 (preferably up to 4) carbon atoms; aralkoxy is preferably mono- or bi-cyclic carbocyclic in the "aryl" portion and contains up to 8 (preferably up to 4) carbon atoms in the alkoxy portion; acylamino is preferably alkanoylamino having up to 8 (preferably up to 4) carbon atoms; halogen is preferably fluorine, chlorine or bromine; and heterocyclic, defining $R_1$, is preferably a 5- or 6-numbered ring in which the 1 or 2 hetero atoms are selected from N, O or S (preferably N or O).

According to the present invention there are further provided processes for the production of compounds of the invention in which (a) an oxazolone of the formula

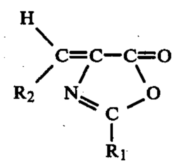

in which $R_1$ and $R_2$ have the above-mentioned meanings, is reacted with a tryptophan derivative of the general formula

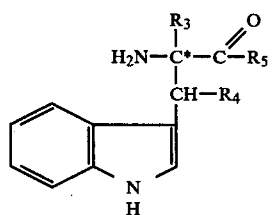

in which $R_3$ and $R_4$ in each case denote hydrogen atoms, $R_5$ has the above-mentioned meaning and C* is in the racemate form or in the D-form or L-form, in the presence of an organic solvent water or mixtures of the two, at temperatures between 0° and 80° C., or (b), for a compound of the general formula (I) in which $R_3$ and $R_4$ denote an additional bond between the two carbon atoms, a saturated oxazolone of the general formula

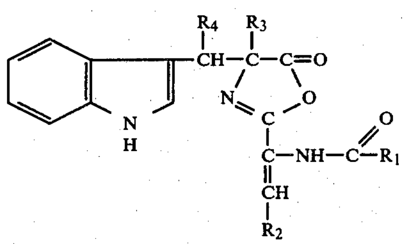

in which $R_1$ and $R_2$ have the above-mentioned meaning and $R_3$ and $R_4$ both denote a hydrogen atom, is oxidised in the presence of an inert organic solvent and of tertiary base, and the product is then saponified in the presence of a diluent containing water, at temperatures between 0° and 70° C., to give a compound of the general formula (I).

The preparation of the compounds of the present invention according to variant (a) is preferably carried out by simply stirring the reaction components of formula (II) and (III) in a suitable diluent.

Suitable diluents are, in particular, those organic liquids which are polar and aprotic and water-miscible. Examples which may be mentioned are acetone, methyl ethyl ketone, diethyl ketone, $C_1$ to $C_4$ aliphatic alcohols, particularly alkanols and cyclic ethers, in particular dioxane and tetrahydrofurane. Acetone and tetrahydrofuran have proved particularly suitable.

If the free aminoacids of the formula (III) are used as the condensation partner for the oxazolone of the formula (II), 1 mol of amino acid and 1 mol of sodium hydroxide are preferably employed per 1 mol of oxazolone. The reaction temperatures can be varied within the stated range; preferably the reaction is carried out between 10° and 30° C.

The reaction time varies and is between 30 minutes and several days, and is preferably one to three hours. Working up is preferably effected by filtering the reaction solution and acidifying the filtrate with a dilute mineral acid. It is particularly preferable to use 1 mol of a mineral acid per 1 mol of sodium hydroxide employed. The reaction products are usually isolated by evaporating off the organic diluent in vacuo, whereupon the reaction product precipitates and is recrystallised from a suitable solvent.

The starting compounds of formula (II) used for the preparation of the compounds of the present invention i.e. the corresponding 2,4-disubstituted 5(4H)-oxazolones, are known from the literature or can be prepared by known methods (see. R. M. Herbst and D. Shemin in Org. Synth. Coll. volume II, 1 (1943)).

The preparative process of the present invention may be illustrated by the reaction of acetylglycine with benzaldehyde. This reaction takes place according to the equation

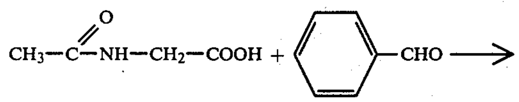

-continued

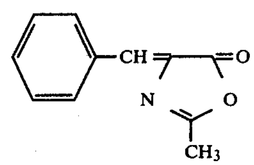

The reaction is preferably effected by mixing the two components in an equimolar ratio in the presence of a condensing agent, preferably acetic anhydride, which at the same time serve as the solvent, and in the presence of a basic component, such as sodium acetate. After allowing the mixture to stand for several hours, it is worked up by diluting with water and recrystallising the 4-benzylidene-2-methyl-5(4H)-oxazolone, which has precipitated, from ethyl acetate/petroleum ether.

The compounds of the general formula (I) according to the invention in which $R_3$ and $R_4$ together represent a bond are prepared, according to process (b), by generally known procedures (see S. Konno et al, Synthesis 1978, 598). The starting material of formula (IV) is preferably prepared by first reacting compounds of the formula (I) in which $R_3$ and $R_4$ both denote a hydrogen atom and $R_5$ denotes a hydroxyl group (prepared by variant a) with a dehydrating agent in an inert organic solvent, thus giving the saturated oxazolone of the formula (IV) which is then reacted according to process variant (b) as described previously.

Dicyclohexylcarbodimide may be mentioned as an example of a dehydrating agent. 2,3-Dichloro-5,6-dicyano-p-benzoquinone may be mentioned as an example of an oxidising agent for process variant (b). 2,4,6-Trimethylpyridine may be mentioned as an example of a tertiary base for process variant (b). Tetrahydrofuran and 2,3,-dimethoxyethane may be mentioned as an examples of solvents.

The hydrolysis is effected by stirring the compound or leaving it to stand with water in the presence of diluents.

Both polar aprotic and protic organic diluents can be used as the diluents. Examples of polar aprotic diluents which may be mentioned are ketones, such as, for example, acetone, methyl ethyl ketone and diethyl ketone, and cyclic ethers (tetrahydrofurane and dioxane). Acetone and tetrahydrofurane are particularly preferred.

Examples of polar protic diluents which may be mentioned are water and $C_1$ to $C_4$ alcohols, such as methanol, ethanol, propanol or isopropanol and all the butanol isomers.

The reaction is preferably carried out in the presence of acid or basic catalysts.

Acid catalysts which are preferably used are strong mineral acids, such as hydrochloric acid or sulphuric acid, or strong organic acids, such as benzenesulphonic acid or toluenesulphonic acid or trichloracetic acid.

Inorganic bases, for example, alkali metal hydroxides, such as sodium hydroxide or potassium hydroxide, have proved suitable basic catalysts. Sodium hydroxide and potassium hydroxide are particularly preferred.

The reaction temperatures for variant (b) can be varied within the stated range, preferably between 10° and 30° C.

Examples of the compounds according to the invention which may be mentioned are: N-acetyldehydrophenylalanyl-L-tryptophan, N-acetyldehydrophenylalanyl-D-tryptophan and N-acetyldehydrophenylalanyl-dehydro-tryptophan.

Compounds of the general formula (I) in which $R_1$ denotes a hydrogen atom, an alkyl group with 1 to 4 carbon atoms, or a phenyl or benzyl radical, $R_2$ denotes a phenyl radical which is optionally substituted by alkyl with 1 or 2 carbon atoms or halogen, $R_3$ and R both denote a hydrogen atom or together represent an additional bond between the two carbon atoms, $R_5$ denotes a hydroxyl group, an alkoxy group with 1 to 4 carbon atoms, a benzyloxy or amino group and n is 1 or 0, or a salt thereof, are of particular interest.

Compounds of the formula (I) in which $R_1$ denotes a methyl group, $R_2$ denotes a phenyl radical, $R_3$ and $R_4$ both denote a hydrogen atom or together represent an additional bond between the two carbon atoms $R_5$ denotes a hydroxyl group and n is 1 may be singled out in particular, of which compounds in which $R_3$ and $R_4$ both denote a hydrogen atom, either in racemic or optically active form are especially preferred.

When administered locally and systemically, the active compounds according to the invention have a histolytic action which depends on the dose. By local, there may be understood in this context the following types of administration: subcutaneous or intracutaneous, administration and in the form of external agents in ointments, gels, lotions, creams, injection solutions and injection suspensions.

By systemic administration there may be understood: intravenous, intraperitoneal, rectal and oral administration, for flushing body cavities and the bladder.

The necroses are usually formed in the immediate region of the points of administration, and in some cases also in regions far removed from these points (lymphogenic). Surprisingly, when the necrotic region breaks open, it is free from putrid material, even over a prolonged period, although feed, faeces, sawdust and other material came into contact with the open wound in the case of the experimental animals.

The necrotic tissue is sharply divided from the surrounding healthy tissue; it has the appearance, macroscopically and microscopically, of being stamped out.

The general behaviour of the experimental animals is not influenced by the size of the necrosis. The total organism is not poisoned.

The $LD_{50}$ of the compounds according to the invention is 400 mg/kg in the case of intravenous injection to rats and mice in an acute experiment. After intraperitoneal administration to mice, the $LD_{50}$ is over 2,000 mg/kg, and is over 1,000 mg/kg in the case of rats.

The present invention also includes the use of the active compounds according to the invention and of pharmaceutical formulations which contain one or more active compounds according to the invention for the treatment of those tissues, in the field of medicine, which prevent and interfere with the course of normal biological functions.

The compounds according to the invention can likewise be employed for resolving moles, atheroma and lipoma and for the removal of deep abscesses, which in certain circumstances are fistulous.

In addition, the compounds according to the invention can be employed for the regeneration of cavernoma and tuberculoma.

The compounds according to the invention can likewise be employed for scar-free regeneration of the substance defects in the case of leprosy and other skin, mucous membrane or epithelium defects of various origin, above all those which are caused by infections by bacteria, fungi and pathogens of tropical diseases, for example, those of leishmaniases, framboesia and pinta.

As stated above, the invention also relates to the use in medicine of the compounds of the invention.

The present invention provides a pharmaceutical composition containing as active ingredient a compound of the invention in admixture with a solid, liquid or liquefied gaseous diluent.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament is dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example groun nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

As an example of an injection solution, the active compounds according to the invention are dissolved in dilute physiologically acceptable bases, if necessary with the aid of solubilising agents, and the solution is brought into an injection form of pH 6.8 to 8.0, in particular 7 to 7.4, by adding physiologically acceptable acids.

Examples of physiologically acceptable bases which may be mentioned are inorganic hydroxides, carbonates and bicarbonates, in particular alkali metal hydroxides, carbonates or bicarbonates, such as those of sodium and potassium.

Examples of physiologically acceptable acids which may be mentioned are organic acids, such as citric acid, oxalic acid, lactic acid, benzoic acid, salicylic acid and acetic acid, or also inorganic acid, for example, dilute hydrochloric or sulphuric acid.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 1 to 90%, usually from 5 to 50% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for dealyed release of the active ingredient. Some, such as capsules, include a protective envelope which renders the portions of the medicament physically discrete and coherent.

The preferred daily dose for administration of the medicaments of the invention is 100 to 2,000 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged, as mentioned previously, that these active compounds will be administered at the site of the disease or systemically, i.e. perorally, parenterally (for example intraperitoneally, intrapleuraly, subcutaneously, intracutaneously, intratumorally and intravenously), rectally or topically, i.e. peritumorally; preferably parenterally. Preferred pharmaceutical compositions and medicaments are therefore those adapted for administration such as parenteral administration. Administration in the method of the invention is preferably parenteral administration.

In general it has proved advantageous to administer amounts of from 1 mg to 100 mg/kg, preferably 2 to 40 mg/kg, of body weight per day to achieve effective results. Nevertheless, it can at times be necessary to deviate from those dosage rates, and in particular to do so as a subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the production of the compounds of the present invention.

EXAMPLE 1

N-Acetyldehydrophenylalanyl-L-trptophan 100 ml of N sodium hydroxide solution are added to a suspension of 18.7 g (0.1 mol) of L-tryptophan in 40 ml of acetone, while stirring, and to the solution formed, a second solution of 20.4 g (0.1 mol) of 2-methyl-4-benzylidene-5(4H)-oxazolone (R. M. Herbst and D. Shemin, Org. Synth. Coll. volume II, 1 (1943)) in 60 ml of acetone is then added. After stirring the reaction solution at room temperature for 2½ hours, it is treated with active charcoal and filtered over kieselguhr and the filtrate is neutralised with 100 ml of N hydrochloric acid. The precipitate which has separated out is filtered off, washed with water and recrystallised from ethanol/water (1:1). Yield: 27.8 g (71% of theory). Melting point: 215° C.

$[\alpha]_D^{20} = -26.3°$ C. (c=0.5, dimethylformamide).

The following compound is prepared similarly:

EXAMPLE 2

N-Acetyldehydrophenylalanyl-D-tryptophan

This compound is obtained analogously to Example 1 from 2-methyl-4-benzylidene-5(4H)-oxazolone and D-tryptophan. Yield: 58.7% of theory). Melting point: 220° to 221° C.

$[\alpha]_D^{20} = +26.3°$ C. (c=0.5, dimethylformamide).

EXAMPLE 3

N-Acetyldehydrophenylalanyl-dehydrotryptophan 2.1 g (10 mmols) of dicyclohexylcarbodimide are added to a suspension of 3.9 g (10 mmols) of N-acetyldehydrophenylalanyl-L-tryptophan in 20 ml of dry tetrahydrofurane at room temperature, whilst stirring. After stirring the mixture for 2 hours and then leaving it to stand overnight in a refrigerator, the dicyclohexylurea which has precipitated is filtered off and washed with tetrahydrofurane. The filtrate is evaporated and the saturated crude oxazolone which remains is dissolved in 80 ml of 1,2-dimethoxyethane (filtered over neutral aluminium oxide in order to be dried). 2.3 g (10 mmols) of 2,3-dichloro-5,6-dicyano-p-benzoquinone and 1.32 ml (10 mmols) of 2,4,6-trimethylpyridine are added successively, whilst stirring. The batch is kept at room temperature for 6 hours and evaporated and the residue is chromatographed on silica gel, from ethyl acetate. The fractions containing the unsaturated oxazolone are evaporated and the residue is extracted by stirring with water and dried.

Yield: 2.2 g (59.5% of theory). Melting point: 207° to 209° C.

11.5 g (30.9 mmols) of the oxazolone, prepared as above, of the title compound are suspended in 80 ml of acetone, and 30.9 ml of 2 N sodium hydroxide solution are added dropwise at room temperature, whilst stirring. The solution formed is kept at room temperature for 1 hour and then diluted with 400 ml of water and extracted with methylene chloride. The precipitate which crystallises out after acidifying the aqueous phase with citric acid is filtered off, washed with water, extracted twice by stirring with ethyl acetate and dried at 100° C.

Yield: 8 g (66.7% of theory). Melting point: 175° to 178° C.

Among the new dehydropeptide salts of the invention, those salts that are pharmaceutically acceptable are particularly important and are preferred, including acid addition and alkali metal salts.

The new free dehydropeptides of the general formula (I) and their salts can be interconverted in any suitable manner; methods for such interconversion are known in the art. Thus, a resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound which is a dehydropeptide of the formula

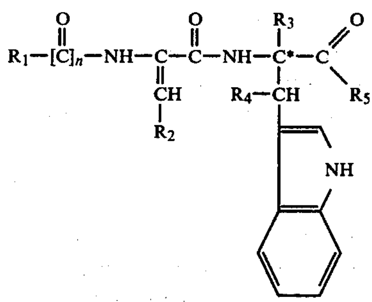

or a salt thereof,
in which $R_1$ denotes a hydrogen atom, an optionally substituted alkyl, alkenyl, aralkyl, aralkenyl aryl, alkoxy group or a heterocyclic ring, $R_2$ denotes a phenyl radical which is optionally substituted by alkyl, aryl, alkoxy, hydroxyl, nitro, amino, acylamino or halogen, $R_3$ and $R_4$ both denote a hydrogen atom, or together denote an additional bond between the two carbon atoms, $R_5$ denotes a hydroxyl group or an optionally substituted alkoxy, aralkoxy or amino group and n is 1 or 0, and in which, when $R_3$ and $R_4$ both denote a hydrogen atom, the centre of asymmetry C* at the substituent $R_3$ is in the racemate form, or in the D-form or L-form.

2. A compound according to claim 1, in which $R_1$ denotes a hydrogen atom, an alkyl group with 1 to 4 carbon atoms or a phenyl or benzyl radical, $R_2$ denotes a phenyl radical which is optionally substituted by alkyl with 1 or 2 carbon atoms or halogen, $R_3$ and $R_4$ both denote a hydrogen atom or together represent an additional bond between the two carbon atoms, $R_5$ denotes a hydroxyl group, an alkoxy group with 1 to 4 carbon atoms, a benzyloxy or amino group and n is 1 or 0.

3. A compound according to claim 1, in which $R_1$ denotes a methyl group, $R_2$ denotes a phenyl radical, $R_3$ and $R_4$ both denote a hydrogen atom or together represent an additional bond between the two carbon atoms, $R_5$ denotes a hydroxyl group and n is 1.

4. A compound according to claim 3, in which $R_3$ and $R_4$ both denote a hydrogen atom, in their racemic form and in their optically active form.

5. A pharmaceutical composition containing as an active ingredient 1 to 90% of a compound according to claim 1 in admixture with a solid, liquid or liquefied gaseous diluent.

6. A pharmaceutical composition of claim 5 in the form of a sterile or physiologically isotonic aqueous solution.

7. A composition according to claim 5 or 6 containing from 5 to 50% by weight of the said active ingredient.

8. A medicament in dosage unit form comprising a compound according to claim 1 in an inert pharmaceutical carrier.

9. A medicament of claim 8 in the form of tablets, pills, dragees, capsules, ampoules or suppositories.

10. A method of treating tissues to provide histolytic effect which comprises administering to warm-blooded animals a histolytically effective amount of an active compound according to claim 1 either alone or in admixture with a diluent or in the form of a medicament.

11. A method according to claim 10 in which the active compound is administered in an amount of 2 to 40 mg per kg body weight per day.

12. A method according to claim 10 or 11 in which the active compound is administered parenterally.

13. A compound according to claim 1 which is N-Acetyl dehydrophenylalanyl-L-tryptophan.

14. A compound according to claim 1 which is N-Acetyl dehydrophenylalanyl-D-tryptophan.

15. A compound according to claim 1 which is N-Acetyl dehydrophenylalanyl-dehydrotryptophan.

* * * * *

UNITED STATES PATENT AND TRADEMARK OFFICE

CERTIFICATE OF CORRECTION

PATENT NO. : 4,285,935

DATED : Aug. 25, 1981

INVENTOR(S) : Eugen Etschenberg et al

It is certified that error appears in the above-identified patent and that said Letters Patent are hereby corrected as shown below:

| | |
|---|---|
| Title Page Assignee | Delete "Bayer Aktiengesellschaft, Leverkusen" and insert --Troponwerke GmbH and Co. KG, Koeln--. |

Signed and Sealed this

*Ninth* Day of *February 1982*

[SEAL]

*Attest:*

GERALD J. MOSSINGHOFF

*Attesting Officer* *Commissioner of Patents and Trademarks*